(12) United States Patent
Griffin et al.

(10) Patent No.: US 8,518,137 B2
(45) Date of Patent: Aug. 27, 2013

(54) MINIATURE ACTIVE STANDOFF CHAMBER

(75) Inventors: Eric J. Griffin, Rancho Palos Verdes, CA (US); Evan H. Griffin, Redondo Beach, CA (US)

(73) Assignee: Raytheon Company, Waltham, MA (US)

( * ) Notice: Subject to any disclaimer, the term of this patent is extended or adjusted under 35 U.S.C. 154(b) by 360 days.

(21) Appl. No.: 12/886,624

(22) Filed: Sep. 21, 2010

(65) Prior Publication Data

US 2012/0067143 A1   Mar. 22, 2012

(51) Int. Cl.
*B01D 46/00* (2006.01)
*F24F 9/00* (2006.01)

(52) U.S. Cl.
USPC ....... 55/385.1; 55/338; 55/DIG. 29; 454/190; 454/191; 454/192

(58) Field of Classification Search
USPC ........... 55/338, 385.1, 385.2, 385.4, DIG. 29; 73/863.23; 454/188, 190, 191, 192
See application file for complete search history.

(56) References Cited

U.S. PATENT DOCUMENTS

| | | | | |
|---|---|---|---|---|
| 4,422,369 | A | * | 12/1983 | Smets ........................... 454/191 |
| 6,884,160 | B1 | * | 4/2005 | Sundholm ..................... 454/191 |
| 7,819,729 | B2 | * | 10/2010 | Rohrer et al. ................. 454/191 |
| 2010/0291856 | A1 | * | 11/2010 | Berben et al. ................. 454/191 |

OTHER PUBLICATIONS

"Environmental & Field Testing Team"; Edgewood Chemical Biological Center; http://www.ecbc.army.mil/ps/svcs_env_field_test_vortex.html; as downloaded on Feb. 15, 2011.

* cited by examiner

*Primary Examiner* — Robert Clemente
(74) *Attorney, Agent, or Firm* — Thorpe North & Western LLP

(57) ABSTRACT

One or more embodiments of a standoff chamber system configured to generate aerosolized clouds, useful in testing or calibrating standoff detectors in a laboratory environment, includes a chamber body having vertically recirculating vortices for generation of the clouds. The standoff chamber further includes a pair of aero-windows configured to surround a pair of apertures in the chamber body, filtering and preventing escape of the cloud, while allowing direct observation of the cloud by standoff detectors.

12 Claims, 4 Drawing Sheets

MINIATURE ACTIVE STANDOFF CHAMBER

BACKGROUND

This disclosure relates generally to standoff detection systems. More particularly, this disclosure may relate to chambers configured to suspend clouds of aerosols for testing and calibration of such systems.

Standoff detection is the remote detection of the presence of a substance. In some cases, the substance to be detected may be aerosolized (i.e. comprise particulates in a cloud). Such remote detection may be advantageous over localized detection, such as through sniffer detectors, in a diverse number of situations, including where the substance is a chemical and/or a biological agent. For example, where the substance is a chemical and/or biological agent used as an aerosolized weapon, remote detection may allow for early warning and response, without those operating the detector already being in a zone of danger. Standoff detection also permits monitoring in areas where localized detectors cannot be feasibly placed, such as over water in a port or on property immediately adjacent to high value strategic assets (e.g. military bases) not under direct ownership of the operating body. Various types of standoff detectors exist, including but not limited to Light Detection and Ranging (LIDAR) standoff detectors. There are currently only a limited number of standoff detectors for chemical and biological threats, notably the Frequency Agile Laser (FAL) and the Joint Biological Standoff Detection System (JBSDS). However, remote sensing of aerosols can be used for other applications using LIDAR and hyperspectral technologies, such as wind shear detection and cloud mapping.

It may be desirable to characterize some standoff detectors based upon their ability to detect signatures of biological or chemical agents at certain concentrations, from a certain distance. This characterization may be useful both for classifying the effectiveness of the detector, and for calibrating the detector. Due to the inherent danger of some biological or chemical agents, simulants may be utilized that approximate the presence of a more hazardous substance, by presenting similar detectable signatures to the detector. A non-exhaustive list of common simulants includes Arizona road dust, powdered egg whites, acetone, polydimethylsiloxanes, and polyethylene glycol.

To generate and isolate an aerosolized cloud of chemical and/or biological agents, or simulants thereof, standoff chambers may be utilized. Depending on the type of detector being tested, different types of chambers suffer from various design inefficiencies. For example, conventional standoff chambers are large structures that are generally immovable. The chambers are constructed in place, necessitating users to bring their detectors to the chamber site in order for them to be tested or calibrated. As an example, the Active Standoff Chamber (ASC), also known as the Vortex Chamber, is located at the Edgewood Chemical Biological Center (ECBC), and measures 20 feet by 24 feet, having a 4 foot large aero-window. One proposed chamber, submitted to the Army's Simulation, Training & Instrumentation Command (STRICOM), was based on the Active Standoff Chamber, but would have been over 100 feet long, utilizing a 10 foot long window. Due to the immense size of prior chamber configurations, value may be found in reducing the size of standoff chambers. For example, a reduced size of chamber may permit the testing of standoff detectors in local laboratory settings, as opposed to large field testing sites. As another example, larger chambers may require a larger amount of simulant or other agent in order to achieve sufficient particulate density for testing purposes. Increased quantities of more hazardous agents present obvious difficulties both from safety and political perspectives. Even some simulants are themselves precursors to chemical or biological weapons, and may be regulated by law or international treaties as to the amount that may be produced (i.e. under nonproliferation agreements). Development of standoff chambers suitable for laboratory use presents a number of challenges, however.

One such challenge in minimizing the size of a standoff chamber is in containing the cloud within the chamber. Some chambers may utilize physical windows, however where the detector being tested is laser based, such windows may necessitate expensive materials such as zinc sulfide or zinc selenide, due to the long wavelengths involved, to minimize scattered returns. While some prior chambers have utilized thin film windows or large tubular constructions, these designs may yield unacceptable scatter or contamination in laboratory settings, or be of an impractical size for a conventional laboratory. For example, the ECBC ASC utilizes a cylindrical geometry, and accordingly its footprint on the ground grows with the square of the path length distance. It is highly advantageous to have a long path-length to more accurately simulate a cloud of aerosol, but the sideways growth of the chamber rapidly eats up valuable laboratory real estate without directly contributing to the testable length.

For certain types of detectors, it may desirable or necessary during calibration or testing for the detector to have an unobstructed view of the cloud (i.e. where observation is not through any transparent shield material), so as to further reduce or eliminate unwanted scatter. One such mechanism to permit unobstructed observation is through the use of aero-windows, which are apertures in the standoff chamber surrounded by a filtering flow of air that is configured to absorb and filter any of the cloud that may exit through the aperture. Such aero-windows present an unobstructed view of the cloud in the chamber, while preventing the cloud from escaping into the surrounding environment. Even though simulants are generally benign, their unrestrained spread is undesirable. In an enclosed laboratory environment, foreign objects and debris is generally strictly controlled, as the spread of even benign particulates through the escape of the cloud may interfere with other experiments.

Another desirable quality in the construction of any size of standoff chamber is the chamber's ability to hold aerosolized particulates in the cloud for long periods of time. In some chambers, loss of suspension of particles in the cloud may result, for example, by the particles entering a low pressure area of the chamber. In some conventional standoff chambers, the chamber can only suspend an aerosol a matter of seconds before the particles drop out, requiring numerous repetitions of tests to obtain sufficient data, adding to test expenses. Chambers such as the ASC improved greatly on prior chamber designs, having the ability to suspend particles on the order of minutes. However, in the ASC, which utilized a horizontal cylindrical airflow to create the cloud, a low velocity zone at the center of the horizontal vortex was created, resulting in an area where particles could fall out of suspension and settle to the chamber floor. This phenomenon affects larger particles more strongly than smaller particles. Such a design, in conjunction with the inherent transfer rate of the particles into the aero-windows, limited the suspension decay time constant of larger particles entrained in the cloud to approximately a minute. Smaller particles, being less affected, would show a concentration decay time constant of approximately five minutes.

What is needed is, among other things, improvements over known standoff chambers, increasing the amount of time that particles can be maintained in a cloud, while being of a design that permits miniaturization for use in a conventional laboratory environment while maintaining a suitable test path length.

SUMMARY

According to an embodiment, a system for containing an aerosol comprises a chamber for the aerosol. The chamber has a pair of opposing apertures defining an unobstructed path extending through the chamber. The system further includes a pair of internal flow generators positioned inside the chamber. Each internal flow generator is associated with one of the pair of opposing apertures. Each internal flow generator is configured to generate substantially vertical internal flows across an associated pair of opposing apertures, on the inside of the chamber. The system further includes a filtering flow generator configured to generate flows across each of the pair of opposing apertures, outside of the chamber. The filtering flows are substantially parallel to the internal flows. The filtering flows are configured to entrain any of the aerosol that exits the containment chamber through the pair of opposing apertures. The filtering flows are filtered by one or more filters after flowing past the pair of opposing apertures.

According to another embodiment, a system for testing a standoff detector comprises a chamber having a first aperture and a second aperture spaced to define an unobstructed path extending through the chamber. The chamber is configured to generally contain an aerosol therein. The system further comprises a first internal flow generator associated with an interior side of the first aperture. The first internal flow generator is configured to produce a first vortex of the aerosol in the chamber. The first vortex has a horizontal axis of revolution approximately perpendicular to the unobstructed path, and includes a first flow, at least a portion of which extends across the interior side of the first aperture. The system further comprises a second internal flow generator associated with an interior side of the second aperture, configured to produce a second vortex of the aerosol in the chamber. The second vortex has a horizontal axis of revolution approximately perpendicular to the unobstructed path, and includes a second flow, at least a portion of which extends across the interior side of the second aperture. The system further includes an external flow generator configured to produce external flows, at least a portion of each of which extends across an exterior side of each of the first and second apertures. The external flows are configured to entrain any of the aerosol that escapes from the chamber through the first or second apertures, and direct said aerosol into one or more filters configured to filter the aerosol from the external flows. The standoff detector is positioned to view the aerosol through the first and second apertures, so as to measure properties of the aerosol.

Other aspects and embodiments will become apparent from the following detailed description, the accompanying drawings, and the appended claims.

BRIEF DESCRIPTION OF THE DRAWINGS

Various features of embodiments of this disclosure are shown in the drawings, in which like reference numerals designate like elements.

DETAILED DESCRIPTION

Figure 2:
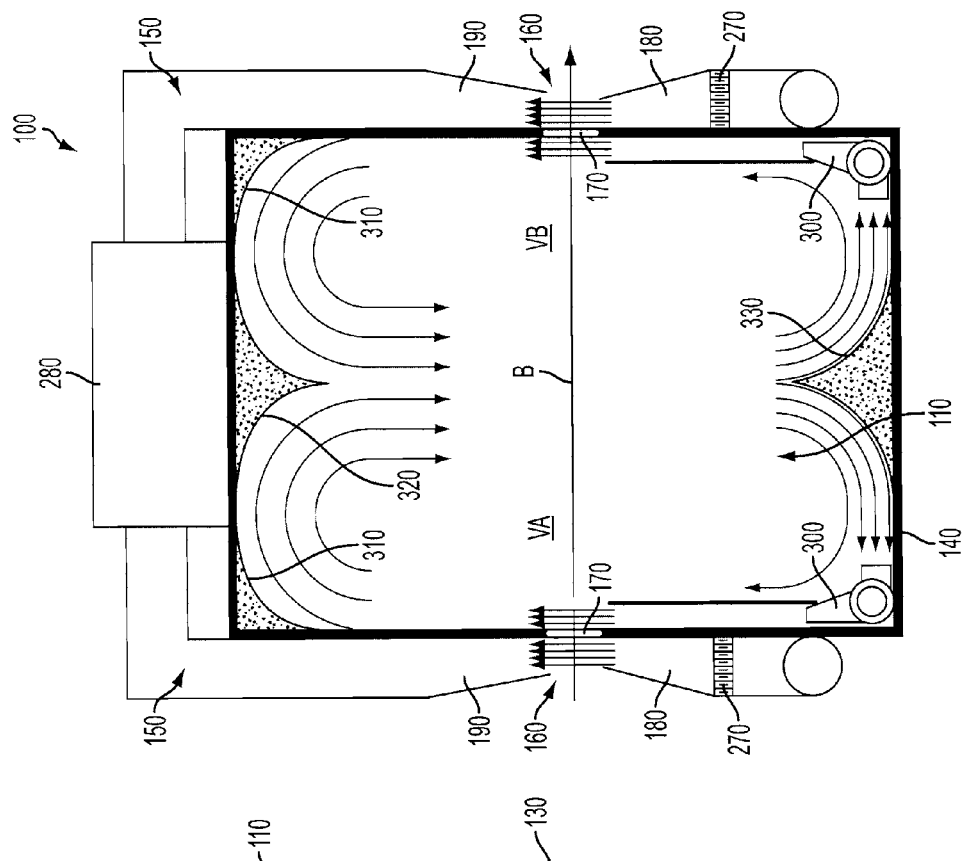
FIG. 2 shows a front cutaway schematic view of an embodiment of the standoff chamber system of FIG. 1, showing inside a chamber body of the standoff chamber system.
Figure 1:
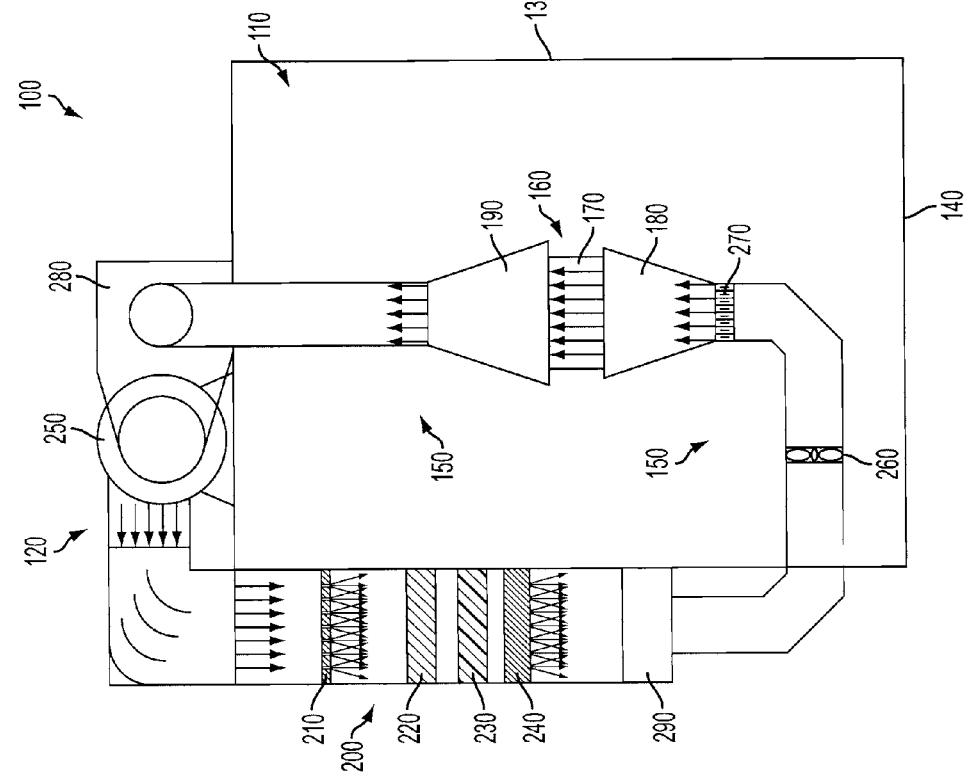
FIG. 1 shows a side schematic view of an embodiment of a standoff chamber system of the present disclosure, using vertical flow vortices to create a cloud.

FIGS. 1 and 2 depict side and front cutaway schematic views of standoff chamber system 100, configured to generate a cloud of aerosol. As seen in FIG. 1, standoff chamber 100 contains chamber body 110 surrounded by circulating filtration system 120, discussed in greater detail below. Chamber body 110 may be of any suitable construction or configuration, which may vary across embodiments. For example, in an embodiment, standoff chamber 100 may be configured to be repeatedly used to test various detectors, and thus chamber body 110 may have a resilient construction, including but not limited to having a chamber body constructed of metal such as but not limited to stainless steel sheeting. In some embodiments, at least some of chamber body 110 may be constructed from polycarbonate material, which may be suitable for the harsh cleaning environments within chamber body 110. In other embodiments, standoff chamber 100 may be designed to utilize low-cost material, for cost-effectiveness of disposability. In such embodiments, chamber body 110 may be constructed from cheaper materials, including but not limited to wood sheet and beams, with lightweight aluminum lining. Such cost effectiveness for disposability may be beneficial where harmful biological or chemical agents are aerosolized in chamber body 110, and standoff chamber 100 is configured to easily be sealed up for incineration or other disposal following testing.

Filtration system 120 is shown in the nonlimiting illustrated embodiment as substantially residing on the top, rear, and sides of chamber body 110. Other configurations of filtration system 120 are possible as well, however the illustrated configuration is presented demonstrate how the configuration may maintain compactness of standoff chamber 100. As shown, front face 130 and/or bottom 140 of chamber body 110 are not covered by ductwork 150 of filtration system 120 in the illustrated embodiment. Ductwork 150 may include any element along the flow path of filtration system 120, such as those described below, or any connecting element for elements of filtration system 120, and may be of any suitable construction or configuration including but not limited to galvanized steel or aluminum. In some such embodiments, ductwork 150 may be absent from front face 130 so that front face 130 of chamber body 110 may be selectively removable, which may permit access to the interior of chamber body 110 for ease of maintenance and cleaning, or for any other reason. In some embodiments, ductwork 150 may be absent from bottom 140 of chamber body 110, so that bottom 140 may provide a flat surface to support standoff chamber 100 and/or to minimize the height of aero-windows 160, described in greater detail below, from the supporting surface. In other embodiments, filtration system 120 may solely reside on the sides of chamber body 110 and one adjacent wall, such as the top, back, or bottom 140 of chamber body 110. In other embodiments, separate filtration systems 120 may be provided for each side of chamber body 110, however in some embodiments may communicate with one another through cabling, wireless transmission, or other means.

As shown, filtration system 120 assists in forming aero-window 160 in standoff chamber 100, so as to allow direct observation of the cloud of aerosol by a standoff detector through aperture 170 in chamber body 110, as is discussed in greater detail below. In the illustrated embodiment of FIG. 1, filtration system 120 is configured to generate a filtering flow of air across aperture 170, from outlet duct 180 to return duct 190, where the filtering flow received by return duct 190 is passed through a plurality of filters in filter module 200. In an embodiment, the filtering flow entering return duct 190 may be characterized as "dirty air." Such dirty air may include ambient air from outside standoff chamber 100, air blown out of outlet duct 180, and air from inside chamber body 110 that is exiting aperture 170. In an embodiment, such as that shown in FIG. 1, outlet duct 180 may be of a different size than connecting ductwork 150, changing in width to exceed a width of aperture 170. Also as shown, return duct 190 may also be of a larger width than aperture 170, and in the illustrated embodiment, is larger in width than the maximal width of outlet duct 180.

Filter module 200 serves to filter the dirty air, and in particular serves to keep particulates of simulant or other agents from the cloud inside chamber body 110 from exiting standoff chamber 100 into the ambient environment. In the non-limiting illustrated embodiment, filter module 200 may comprise perforated plate 210, which may smooth out the filtering flow of dirty air, so as to prevent harm to other filters in filter module 200. Filter module 200 may include pre-filter 220, which may capture thick or heavy particulates from the dirty air that may be easily trapped by conventional filtering. In an embodiment, filter module 200 may include charcoal filter 230 to filter out finer biological or chemical agents that may be in the dirty air. In some embodiments, filter module 200 may include HEPA filter 240, which may filter other fine particulates. Other filters may also be present in filter module 200, to prevent escape of undesirable particulates from inside chamber body 110. In an embodiment, filter module 200 may be opened for removal of the filters therein, so that such filters may be cleaned or replaced.

In the illustrated embodiment, the filtering flow of air is recirculated after filtration back to outlet duct 180. In an embodiment, such filtered air may be characterized as "filtered air." In such an embodiment, the filtering flow is generated by filtering system blower 250, which pulls dirty air from return duct 190 into filter module 200 for filtration. Filtering system blower 250 may be of any suitable configuration, and in an embodiment may be of a totally enclosed, fan cooled configuration. In an embodiment, a filtering flow of filtered air from filter module 200 may pass through flow balance adjust fan 260, as is discussed in greater detail below, so that a desired flow rate of filtered air may be obtained in aero-window 160. Although in an embodiment filtration system 120 could simply vent the filtered air into the environment, this approach is less efficient, as it does not take advantage of recirculated filtering through filter module 200. This lack of recirculation may result in a shorter effective lifetime for filter module 200, due to a constant input of unfiltered air into aero-window 160.

In an embodiment, flow straightener 270 may straighten the filtering flow of filtered air or ambient air prior to passing through outlet duct 180, for passage over aperture 170 of aero-window 160. Flow straightener 270 may be of any construction or configuration, including but not limited to slots, holes, honeycomb, screens, or any other shape which may drive the filtering flow across aperture 170 in a substantially parallel direction to that of aperture 170. In an embodiment, flow straightener 270 may be immediately prior to or part of outlet duct 180, so that flow conditioning is in line with the flow for aero-window 160. In an embodiment, flow balance adjust fan 260 may adjust the rate of the filtering flow driven by filtering system blower 250, prior to the filtering flow entering flow straightener 270, so as to slow down or speed up the filtered flow rate across aero-window 160 as necessary to best match an internal flow rate of the cloud inside chamber body 110, as is discussed in greater detail below. In an embodiment, flow balance adjust fan 260 may communicate with flow sensors (described in greater detail below) inside chamber body 110, and be configured to automatically adjust the filtering flow in filtration system 120. In other embodiments, air balance adjust fan 260 may be manually tunable, to account for effects of ductwork 150, filter module 200, or other elements in filtration system 120 on the rate of the filtering flow over aperture 170.

In an embodiment, standoff chamber 100 may have corresponding aero-windows 160 on opposing sides of chamber body 110. In an embodiment, a single filtering system blower 250 and filter module 200 may be common to both aero-windows 160. In the illustrated embodiment, return manifold 280 may connect ductwork 150 from return duct 190, so that the filtering flow may reach common filtering system blower 250 and common filter module 200. In an embodiment, common outlet manifold 290 may divide filtered air from filter module 200 back to either side of chamber body 110, for recirculation through outlet duct 180.

Turning to FIG. 2, a front cutaway schematic view of an embodiment of standoff chamber 100 is shown, in particular where front face 130 of chamber body 110 would be removed. Shown on the exterior of chamber body 110 is outlet manifold 280 connecting ductworks 150 associated with each of aero-windows 160 on the left and right side of chamber body 110. As shown, aero-windows 160 are aligned such that beam from a standoff detector traveling along beam-line B between aero-windows 160 may pass through standoff chamber 100, to view a cloud in chamber body 110 unobstructed. In other embodiments, wherein an unobstructed view through the cloud is unnecessary, standoff chamber 100 may have only a single aero-window 160, and thus would not need return manifold 280 and outlet manifold 290. From this side view of aero-windows 160, it is seen that in the illustrated embodiment, outlet duct 180 may be directed inward towards chamber body 110, compressing the filtering flow and providing a favorable pressure gradient as it approaches aperture 170. Also as shown, return duct 190 on the opposite side of aperture 170 may expand outward, such as back towards the thickness of connecting ductwork 150. In an embodiment, the minimum thickness of return duct 190 may be larger than the minimum thickness of outlet duct 180, sized so that the sum output of air flowing from outlet duct 180 is fully captured but entrained ambient air is not. In an embodiment, such as one without a closed filtering flow loop, the larger size of return duct 190 as compared to outlet duct 180 may allow for an external entrained flow from the ambient air outside standoff chamber 100 to join the filtering flow in filtration system 120.

Shown inside chamber body 110 of the illustrated embodiment are vortices V, such as vortex VA and vortex VB, formed by the circulation of air by associated internal blowers 300. As shown, the axes of vortices V are horizontally oriented approximately perpendicular to the beam-line B. Internal blowers 300 are configured to direct an internal flow upward, against the pull of gravity, wherein it may contact a portion of or a structure inside chamber body 110, and may generally fall, creating vortices V. Internal blowers 300 may be of any suitable construction or configuration, and in an embodiment may be of a totally enclosed, fan cooled configuration. In an embodiment, internal blowers 300 may be explosion proof, such as if large concentrations of particulates or volatile simulants are to be aerosolized inside chamber body 110. In an embodiment, the internal flow may be the portion of vortex VA or VB over aperture 170. In an embodiment, internal blowers 300 are located along bottom 140 of chamber body 110, near the sidewalls comprising associated apertures 170. In an embodiment, internal blowers 300 may extend substantially the entire length of chamber body 110, even in embodiments where the length of aperture 170 is significantly smaller. As one non-limiting example, where aero-window 160 and thus aperture 170 is approximately a six inch square, chamber body 110 may be approximately three feet long by three feet wide by five feet tall, and thus internal blowers 300 may be approximately three feet long, extending along the width of chamber body 110, alongside aero-window 160.

In an embodiment, the interior of chamber body 110 may be configured without excessive flow conditioning, so that turbulence may maintain suspended aerosol in the generated cloud. In an embodiment, such as those illustrated, flow conditioning may be present between internal blowers 300 and the bottom of aperture 170, so that the internal flow may be smooth at aero-window 160. As an example, such flow conditioning may include screens, slots, honeycomb, or other channels to straighten the internal flow from internal blowers 300 as the internal flow crosses aperture 170 inside chamber body 110. Better matching of the internal flow with the filtered air flow results in less transfer across aero-window 160, and correspondingly decreases the rate at which the concentration of aerosol decreases within chamber body 110. In an embodiment, screens and filters may be used to further smooth the internal flow, provided that the screens and filters do not serve to entrap the aerosol or would otherwise adversely interact with the aerosol.

In some embodiments, other flow conditioning may be present around the interior of chamber body 110, so as to generally direct vortices V. In an embodiment, such general direction may still be configured to permit turbulent flow. In a non-limiting embodiment, the corners of chamber body 110 opposite of internal blowers 300 (i.e. at the top of chamber body 110) may comprise corner flow shapers 310, configured to redirect the internal flow of the cloud inside chamber body 110 after it passes over aperture 170 in a curve along the top of chamber body 110. In a non-limiting embodiment, vortex VA and vortex VB are separated by top flow shaper 320 and bottom flow shaper 330, each forming mirrored curves, so that the internal flow coming from associated corner flow shapers 310, are redirected back to internal blowers 300 for recirculation, thus forming each vortex VA and VB of the cloud. In an embodiment, the length of corner flow shapers 310, top flow shaper 230, and bottom flow shaper 330 may extend the entire width of chamber body 110. In an embodiment, vortex VA and vortex VB may be approximately cylindrical along the width of chamber body 110, bounded on either end by front face 130 and the back of chamber body 110. In an embodiment, additional corner flow shapers 310 may be positioned at the bottom corners of chamber body 110. In such an embodiment, internal blowers 300 may be configured to generate a horizontal flow against corner flow shaper 310 at the bottom of chamber body 110, which may redirect the flow upwards in a generally vertical direction. In an embodiment, ducting associated with internal blowers 300 and/or corner flow shapers 310 may extend towards apertures 170 in aero-windows 160, and may assist in maintaining straight or smooth internal flow across the aero-window aperture 170.

In an embodiment, each of internal blowers 300 are configured to circulate associated vortices VA and VB such that internal flows inside chamber body 110 are in the same generally linear direction across each aperture 170. Such a configuration may be useful to allow the filtering flows across each aperture 170 to be in the same direction as the internal flows, without requiring convoluted ductwork 150 to reverse the filtering flow for opposing aero-windows 160. This simpler configuration may cut down on the packaging of standoff chamber 100 used to permit connections to common filtering system blower 250 and filter module 200. In an embodiment, internal blowers 300 may be positioned at bottom 140 of chamber body 110 so as to capture and flow any particulates of the cloud that fall out of vortices VA or VB. In an embodiment, bottom flow shaper 330 may be shaped to direct the particulates into inlets of internal blowers 300, which may push the particulates back into the cloud through outlets of internal blowers 300. In an embodiment, bottom flow shaper 330 may be centered at a common peak, and extend a curve to each of internal blowers 300, so as to reduce or eliminate an area where particulates may settle out when they fall out of vortices VA or VB by the pull of gravity. In an embodiment, the shape of internal blowers 300 may be configured to reduce or eliminate the ability of particulates to settle on internal blowers 300, for example by including a slope to direct particulates falling onto internal blowers 300 into the inlets of internal blowers 300 for recirculation in the vortices VA or VB.

In an embodiment, the shape of internal blowers 300, corner flow shapers 310, top flow shaper 320, and/or bottom flow shaper 330 may include non-uniformities configured to encourage mixing of particulates in the clouds of vortices VA and VB. Such mixing may occur away from the area of internal flow in front of aperture 170 in chamber body 110, so as to prevent excessive transfer of particulates through aperture 170, for attempted capture by filtration system 120. In an embodiment, such non-uniformities may encourage turbulence and collisions of internal flows, which may create a tendency for particulates to stay suspended in vortices VA and VB.

Figure 3:
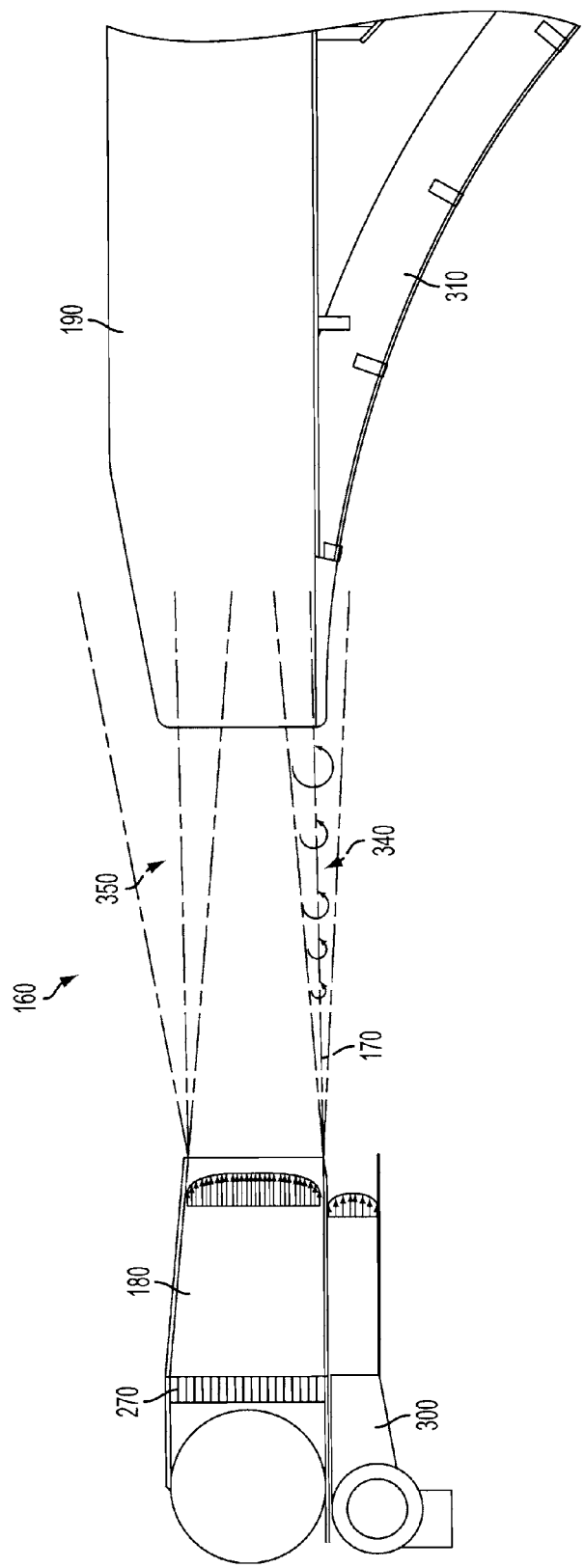
FIG. 3 shows an isolated view of an aero-window separating the chamber body from the standoff chamber system's surrounding environment, according to an embodiment of the present disclosure, illustrating the mixing of air flows therein.

Turning to FIG. 3, an isolated schematic view highlighting filtering and internal flows at aperture 170 is presented to illustrate how aero-windows 160 prevent migration of particulates from the cloud inside chamber body 110 to the outside of standoff chamber 100. As illustrated, once internal flows from internal blower 300 and filtering flows through outlet duct 180 converge in a substantially parallel direction at aperture 170, mixing may occur between the internal flow and the filtering flow in internal/aero-window mixing region 340. Likewise, mixing may occur at aperture 170 between the filtering flow and the ambient air outside of standoff chamber 100, such as that in the external entrained flow in embodiments of standoff chamber 110 configured to receive such a flow. As shown, the mixing between the filtering flow and the ambient air may occur in external/aero-window mixing region 350. As shown, internal/aero-window mixing region 340 and external/aero-window mixing region 350 expand along the direction of the internal flow and the filtering flow. As shown, the mixing regions 340 and 350 do not meet within aero-window 160 (i.e. at aperture 170), and only meet, if anywhere, inside return duct 190. The separation of internal/aero-window mixing region 340 and external/aero-window mixing region 350 along aperture 170 prevents particulates in the internal flow from mixing with the ambient air until after the mixed flow is restrained by return duct 190, and is part of the dirty air in the filtering flow that is driven towards filtering module 200.

As noted above, in an embodiment, the filtering flow in filtration system 120 and the internal flow inside chamber body 110 may approximate one another in rate at aero-window 160. In one non-limiting embodiment, the rate of the filtering flow and/or the internal flow may be approximately 10-20 MPH at aero-window 160. One reason such equivalence of flow rates is desirable is that the width of internal/aero-window mixing region 340 and external/aero-window mixing region 350 increase at a greater rate, potentially creating eddies and other vortices within mixing regions 340 and 350, all of which may contribute to the loss of particulates from the internal flow out of standoff chamber 100. The slower cones of mixing regions 340 and 350 grow, the more likely it is that mixing therebetween will occur inside return duct 190. In some cases, if the filtering flow is at a different rate than that of the internal flow, undesirable pressure may built within chamber body 110, until the pressure is released by expelling particulates through aero-windows 160, which depending on the angle of expulsion might not be captured by filtration system 120.

As noted, flow balance adjustment fans 260 may fine tune the flow rate of the filtering flow, which is generally created by filtering system blower 250. Such fine tuning may account for variations in the flow rate of the filtering flow, such as minute differences between the flow paths of the filtering flow through ductwork 150 associated with each opposing aero-window 160, more efficiently than alternatives, such as baffles, which choke the filtering flows. In some embodiments, flow balance adjustment fans 260 may be responsive to sensors inside chamber body 110 and/or filtration system 120. For example, in an embodiment chamber body 110 may contain one or more sensors configured to measure the flow rate of the internal flow. Such sensors may be of any suitable construction or configuration, including but not limited to a high fill manometer or an impeller fan driven sensor.

In various embodiments, such flow rate sensors may be fixed inside chamber body 110 throughout the operation of standoff chamber 100 for the testing of standoff detectors. In other embodiments, flow rate sensors may be utilized in chamber body 110 for testing or calibrating standoff chamber 100, such as to periodically adjust the flow rate of the external flow, but is removed during normal operation of standoff chamber 100. In some embodiments, it may be desirable to not fix the sensors into chamber body 110. As an example, if standoff chamber 100 is configured to be quickly sealed for disposal after testing, such sensors would otherwise be lost during disposal if fixed into standoff chamber 100. As another example, if the simulant being aerosolized in the cloud in chamber body 110 is oily or may otherwise harm the flow rate sensors, then it may be desirable to remove such sensors prior to addition of the particulate for generation of the cloud.

In some embodiments, the flow rate sensors may be configured to adjust not only flow balance adjustment fans 260, but also or alternatively adjust the flow rate produced by filtering system blower 250 and/or internal blowers 300. In some embodiments, filtration system 120 and chamber body 110 both have flow rate sensors. In some such embodiments, one or more of filtering system blower 250, flow balance adjustment fans 260 or internal blowers 300 may be configured to adjust the filtration flow rate and/or the internal flow rate, so as to optimize the formation of the could inside chamber body 110, and prevent loss of the cloud through aero-windows 160.

In some embodiments, standoff chamber 100 may include one or more sensors configured to measure a particle count in the internal flow. In some embodiments such sensors may be configured to detect a loss of particulate in the cloud inside chamber body 110. In an embodiment, standoff chamber 100 may be configured to automatically replenish particulates in the cloud when a particle count inside chamber body 110 drops below a threshold value. In an embodiment, the loss of particulates may be from the loss of particulates through aero-windows 160 and/or particulates which fall onto a surface in chamber body 110 (such as bottom 140 or bottom flow shaper 330), but are not drawn back into vortices VA or VB by internal blowers 300. In an embodiment, chamber body 110 may comprise one or more particulate injectors. In some embodiments, the particulate injectors may be positioned at the top and/or sides of chamber body 110, and configured to selectively and/or periodically inject an amount of particulate into the internal flow of the cloud.

In some embodiments, insertion of particulate into standoff chamber 100 may be performed manually. In an embodiment, particulates, such as simulants or biological or chemical agents may be poured into chamber body 110 through aero-windows 160, or through another aperture in chamber body 110. In an embodiment, chamber body 110 may comprise a double door "air-lock" aperture, such that insertion of particulates into the internal flow does not cause unwanted dispersion of the particulates through the aperture if internal blowers 300 are producing the internal flow at the time of the insertion. In an embodiment, a separate amount of particulate may be inserted into chamber body 110 for each of vortex VA and vortex VB. In an embodiment, the amount of particulate in chamber body 110 may range from approximately one million particles per cubic foot down to approximately 5000 particles per cubic foot, depending on a desired particle density for the cloud in chamber body 110.

In an embodiment, standoff chamber 100 may be configured to run filtering system blower 250 for a period of time after internal blowers 300 are turned off, so as to continue to filter any of the cloud as it exits aperture 170 as the internal flow of the cloud in vortices V slows, and the particulates settle. In an embodiment, aero-windows 160 may comprise shutters configured to cover apertures 170 once the standoff chamber 100 is turned off. As noted above, such shutters may be used to seal standoff chamber 100 if standoff chamber 100 is configured as disposable following testing. In other embodiments, wherein standoff chamber 100 is designed to be reusable, such shutters may isolate standoff chamber 100 so that particulates may settle, or so that standoff chamber 100 may be relocated for cleaning, which may further reduce a risk of laboratory contamination. In an embodiment, filtering system blower 250, flow rate adjustment fans 260 and/or internal blowers 300 may operate to evacuate particulates down to below a threshold level inside chamber body 110, or to operate for a predetermined amount of time, before standoff chamber 100 is turned off.

In an embodiment standoff chamber 100 may include an uninterruptable power supply configured to continue to run one or more of filtering system blower 250, flow rate adjustment fans 260, and/or internal blowers 300 for a period of time following an unexpected or premature loss of external power. In an embodiment, internal blowers 300 may stop upon loss of external power, while the uninterruptable power supply allows at least filtering system blower 250 to operate to capture and flow through filtration system 120 particulates that may exit through aperture 170 until the particulates in side chamber body 110 settle towards bottom 140 or are depleted through aperture 170. In some embodiments, shutters may be configured to cover aperture 170 in the event of a loss of external power. In an embodiment, the shutters may be configured to close automatically upon loss of external power. In another embodiment, the shutters may be configured to close upon the switch of power from external power to the uninterruptable power supply.

Figure 4A:
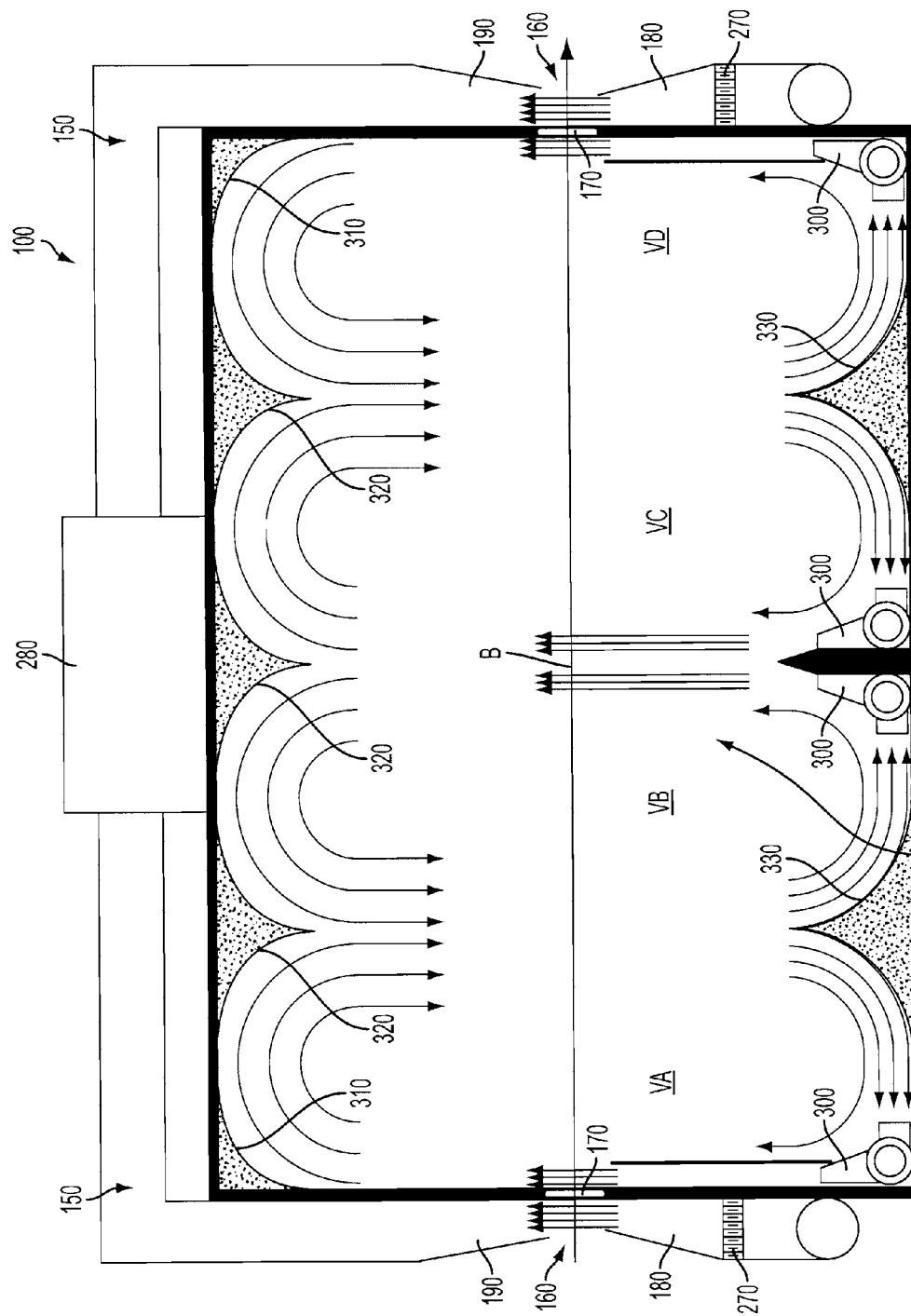
FIGS. 4A-B show front cutaway schematic views of embodiments of the standoff chamber system of the present disclosure, forming additional vertical vortices to create a longer cloud path-length.
Figure 4B:
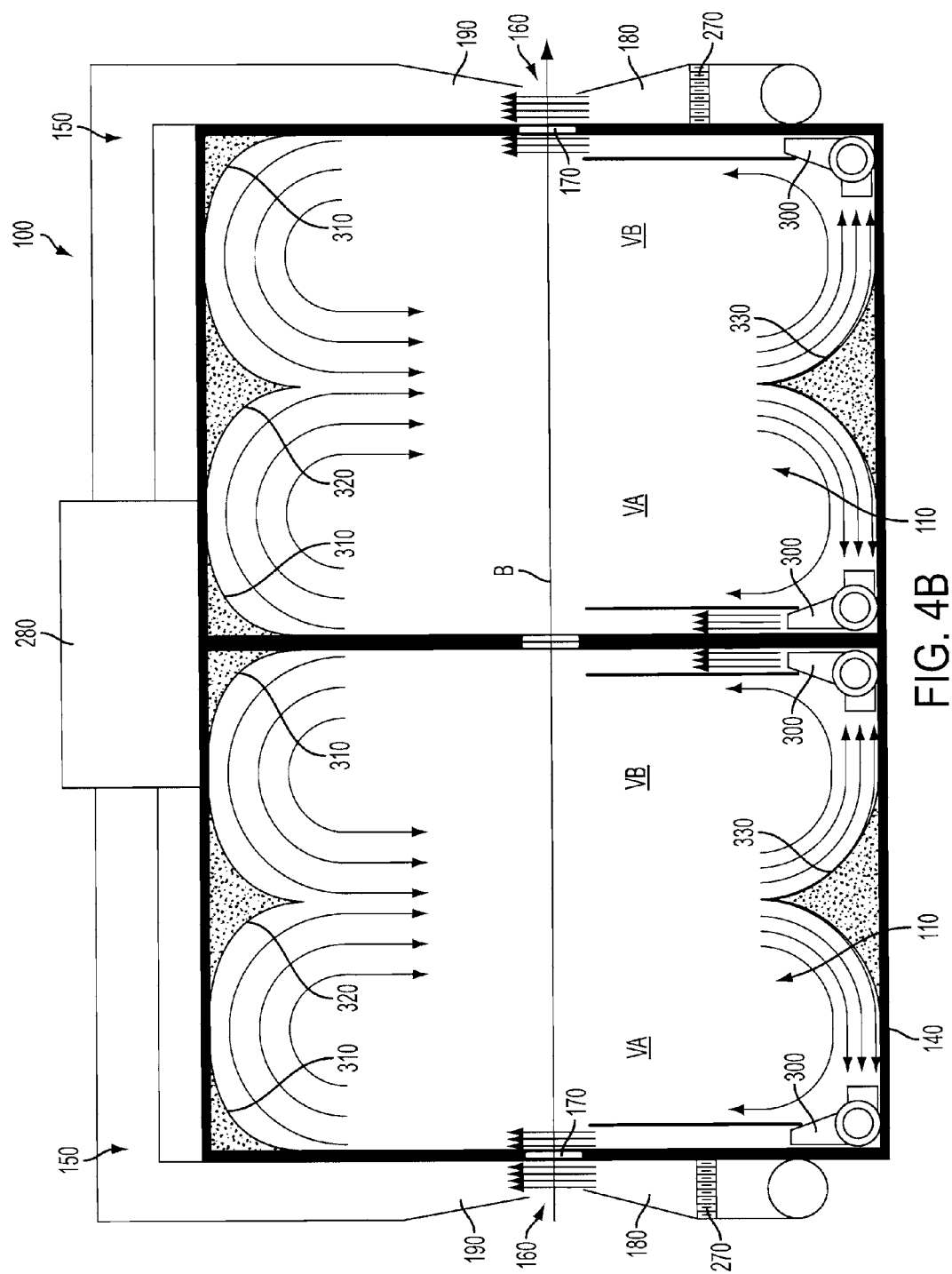

Turning now to FIGS. 4A-B, the scalable nature of some embodiments of standoff chamber 100 is depicted. For example, to increase the size of the cloud from the perspective of a standoff detector, multiple standoff chambers 100, or one or more elongated or aligned chamber bodies 110 having additional vortices V may be utilized. In an embodiment, such elongation or alignment of standoff chambers 100 may result in the additional consumption of space in the elongated or aligned length direction, increasing the thickness of the cloud viewed through aero-windows 160, while not consuming additional floor or laboratory space in the height or width direction.

As seen in FIG. 4A, an elongated chamber body 110 may be utilized, having additional vortices V formed therein. As shown, vortices VA and VB may be joined with additional vortices VC and VD to create a longer cloud through which beam B from a standoff detector may traverse. In other embodiments, additional vortices V may be added, for further expansion to the thickness of the cloud inside chamber body 110. In the illustrated embodiment, aero-windows 160 are present at either extremity of elongated chamber body 110, wherein ductwork 150 connects both aero-windows 160 to return manifold 280. In an embodiment, an even number of vortices V are provided, such that the internal flow across both apertures 170 are in the same direction, simplifying ductwork 150 used to provide the filtering flow from outlet duct 180, so that such ductwork 150 does not need to be in the inverse direction. As shown in the figure, in an embodiment internal blowers 300 in the middle vortices VB and VC may back into one another, respectively redirecting vortices VB and VC towards top flow shaper 320, where they split in opposing directions. In an embodiment, a common internal blower may be used for vortices VB and VC, having respective inlets to receive flows from each of vortices VB and VC, but having a common outlet flow that is split by top flow shaper 320 in the middle of vortices VB and VC. In an embodiment where internal blowers 300 in middle vortices VB and VC are separate bodies, internal blowers 300 may be immediately adjacent to one another, so as to prevent space between them where particulates may settle. In an embodiment, standoff chamber 100 may have multiple insertion points for simulants and/or other agents. In an embodiment, there may be at least as many insertion points as there are vortices V.

In other embodiments, such as that shown in FIG. 4B, multiple chamber bodies 110 may be aligned and coupled as modules, framed by ductwork 150 and aero-windows 160 at opposite extremities of the combined standoff chamber 100. In such embodiments, the intermediate vortices V are formed by the combination of multiple vortices VA and VB. For example, in FIG. 4B, the middle vortices of standoff chamber 100 are formed by vortex VB of the left chamber body 110, and vortex VA of the right chamber body 110.

In some embodiments, multiple standoff chambers 100 may be positioned such that aero-windows 160 are aligned, so that ambient air is present between sections of cloud inside chamber bodies 110. Such a configuration having spacing of ambient air may be useful for a number of purposes, including but not limited to performing range gating, or reenacting atmospheric anomalies within what would appear to the standoff detector being tested or calibrated as a single cloud. In an embodiment wherein multiple standoff chambers 100, each having opposing aero-windows 160, are aligned, each individual standoff chamber may have any number of vortices V, as described above.

While certain embodiments have been shown and described, it is evident that variations and modifications are possible that are within the spirit and scope of the inventive concept as represented by the following claims. The disclosed embodiments have been provided solely to illustrate the principles of the inventive concept and should not be considered limiting in any way.

What is claimed is:

1. A system for containing an aerosol comprising:
   a chamber for the aerosol having a pair of opposing apertures defining an unobstructed path extending through the chamber;
   a pair of internal flow generators positioned inside the chamber, each internal flow generator associated with one of the pair of opposing apertures, each internal flow generator configured to generate substantially vertical internal flows across the associated one of the pair of opposing apertures, inside the chamber;
   a filtering flow generator configured to generate filtering flows across each of the pair of opposing apertures, outside the chamber, substantially parallel to the internal flows;
   wherein the filtering flows are configured to entrain any of the aerosol that exits the containment chamber through the pair of opposing apertures; and
   wherein the filtering flows are filtered by one or more filters after flowing past the pair of opposing apertures.

2. The system of claim 1, wherein the rate of each filtering flow is configured to equal a rate of the internal flows.

3. The system of claim 1, wherein the filtering flows are directed through ductwork surrounding each of the pair of opposing apertures outside of the chamber.

4. The system of claim 3, wherein the ductwork associated with each of the pair of opposing apertures comprise a fan configured to adjust a rate of each filtering flow associated with each of the pair of opposing apertures.

5. The system of claim 4, further comprising one or more flow sensors configured to measure the rate of internal flow, and adjust a speed of each fan to increase the rate of each filtering flow to approximate a rate of the internal flows.

6. The system of claim 1, further comprising a manifold configured to combine each filtering flow to flow together through the one or more filters.

7. The system of claim 1, wherein the external flows are recirculated across each of the pair of opposing apertures after being filtered by the one or more filters.

8. The system of claim 1, further comprising one or more additional internal flow generators spaced between the pair of internal flow generators and configured to generate additional substantially vertical internal flows across the unobstructed path.

9. The system of claim 8, wherein each of the substantially vertical internal flows and each of the additional substantially vertical flows are associated with one or more of a plurality of vortices having a horizontal axis of revolution approximately perpendicular to the unobstructed path.

10. A system for testing a standoff detector comprising:
    a chamber having a first aperture and a second aperture spaced to define an unobstructed path extending through the chamber, the chamber configured to generally contain an aerosol therein;
    a first internal flow generator associated with an interior side of the first aperture, configured to produce a first vortex of the aerosol in the chamber, the first vortex having a horizontal axis of revolution approximately perpendicular to the unobstructed path and including a first flow extending across at least a portion of the interior side of the first aperture;

a second internal flow generator associated with an interior side of the second aperture, configured to produce a second vortex of the aerosol in the chamber, the second vortex having a horizontal axis of revolution perpendicular to the unobstructed path and including a second flow extending across at least a portion of the interior side of the second aperture; and an external flow generator configured to produce external flows, at least a portion of each of which extends across an exterior side of each of the first and second apertures, the external flows configured to capture any of the aerosol that escapes from the chamber through the first or second apertures, and direct said aerosol into one or more filters configured to filter the aerosol from the external flows;

wherein the standoff detector is positioned to view the aerosol through the first and second apertures, so as to measure properties of the aerosol.

11. The system of claim 10, wherein a flow rate for the first flow and/or the second flow and a flow rate for the external flow associated with each aperture may be adjusted to approximate one another.

12. The system of claim 11, further comprising a pair of flow adjustment fans associated with each of the external flows associated with each of the first and second apertures, configured to adjust the flow rate thereof.

* * * * *